United States Patent [19]

Macaudiere et al.

[11] Patent Number: 5,501,733
[45] Date of Patent: Mar. 26, 1996

[54] RARE EARTH METAL SULFIDE PIGMENTS COMPRISING FLUORINE VALUES

[75] Inventors: Pierre Macaudiere, Asnieres/Seine; Jorge Morros, Turckheim; Jean-Michel Tourre, Croissy S/Seine; Alain Tressaud, Pessac, all of France

[73] Assignee: Rhone-Poulenc Chimie, Courbevoie Cedex, France

[21] Appl. No.: 257,823

[22] Filed: Jun. 9, 1994

[30] Foreign Application Priority Data

Jun. 9, 1993 [FR] France ................... 93 06899

[51] Int. Cl.$^6$ .............. C01F 1/00; C01F 17/00; C04B 35/50
[52] U.S. Cl. ............ 106/461; 106/400; 106/401; 106/451; 423/263; 423/265; 423/266
[58] Field of Search ............ 106/451, 461, 106/403, 400, 401; 423/263, 265, 266

[56] References Cited

U.S. PATENT DOCUMENTS 4,545,967 10/1985 Reynolds et al ............ 423/263

FOREIGN PATENT DOCUMENTS 2084478  5/1993  Canada .
0203838  3/1986  European Pat. Off. .
493436   2/1976  U.S.S.R. .

OTHER PUBLICATIONS

Chemical Abstract 84:107942 of SU 493436, Markovskii et al., Nov. 30, 1975.
Derwent Abstract 76–69998x/37 of Su 493436–A Feb. 26. 1976.

Primary Examiner—Mark L. Bell
Assistant Examiner—Scott L. Hertzog
Attorney, Agent, or Firm—Burns, Doane, Swecker & Mathis

[57] ABSTRACT

Fluoridated particulates, especially external face surface-fluoridated particulates of the rare earth metal sesquisulfide pigments/colorants, advantageously encapsulated within a coating layer of at least one transparent oxide or hydrate thereof, e.g., silica, have improved chromatic properties and are well suited for the coloration/pigmentation of a wide variety of materials and substrates, for example paints, plastics, resins, varnishes, rubbers, ceramics, glazes, papers, inks, leathers, cosmetics, dyes, coatings, etc.

49 Claims, No Drawings

RARE EARTH METAL SULFIDE PIGMENTS COMPRISING FLUORINE VALUES

BACKGROUND OF THE INVENTION

1. Field of the Invention

The present invention relates to the fluoridation of inorganic pigment colorants based on rare earth metal sesquisulfides to enhance the coloration thereof.

This invention also relates to novel inorganic pigment colorants, per se, based on rare earth metal sesquisulfides and having improved chromatic characteristics, prepared via the above fluoridation process, as well as to the use of such novel pigments for the coloration of a wide variety of substrates.

2. Description of the Prior Art

It is known to this art that inorganic pigments/colorants are currently widely used for the coloration of a variety of substrates in many industries, especially in those of paints, plastics and ceramics. For such applications, the properties of, inter alia, intrinsic color, coloring power and opacifying power, thermal stability, chemical stability, dispersibility (ability of a product to properly disperse in a given medium) and absence of toxicity, constitute particularly significant criteria to be considered in the selection of a suitable pigment.

The rare earth metal sesquisulfides, of general formula $M_2S_3$ in which M represents at least one rare earth metal, are compounds per se well known to this art and described in numerous publications. Moreover, the use of same as pigments/colorants for the coloration of various substrates, such as, for example, plastics, paints and others, is generally described in EP-A-0,203,838, assigned to the assignee hereof.

Additionally, various pigments based on rare earth metal sesquisulfides possessing improved properties (color or thermal and/or chemical stability in particular) are described in FR-91/14,988 and FR-93/04,544, also assigned to the assignee hereof. In said '988 application, for improving the chromatic characteristics of such compounds, pigments based on rare earth metal sesquisulfides are described which have the distinctive feature of additionally containing at least one alkali metal and/or alkaline earth metal element, at least a fraction of which is occluded in the crystal lattice of said sesquisulfides (doped sesquisulfides).

The '544 application, describing improvements at the level of thermal and/or chemical stability, relates to composite inorganic pigments of core/shell type including a substrate based on doped sesquisulfides as indicated above and of a protective layer based on a transparent oxide deposited onto and coating the surface of the substrate.

Nonetheless, need continues to exist in this art for pigments having even more improved characteristics, especially in respect of the chromaticity thereof.

SUMMARY OF THE INVENTION

Accordingly, a major object of the present invention is the provision of an improved process for enhancing the chromatic properties of pigments based on rare earth metal sesquisulfides.

Another object of the present invention is the provision of a novel class of inorganic colorants/pigments presenting, among other advantages, markedly improved chromatic characteristics, optionally, improved chemical and thermal stability, and an absence of toxicity, such novel colorants/pigments being well suited for the coloration of a wide variety of substrates.

Yet another object of this invention is the provision of a process for the preparation of the aforesaid novel class of colorants/pigments which is simple, economical, reproducible, controlled and suitable for production on an industrial scale.

As utilized herein, by the term "rare earth metal sesquisulfide" are intended compounds of the general formula $M_2S_3$ in which M is at least one rare earth metal. Also, the term "rare earth metal(s)" connotes, singly or in admixture, all of the elements of the lanthanide family having an atomic number ranging from 57 to 71, inclusive, as well as yttrium which has an atomic number of 39. Such rare earth metal sesquisulfides are especially described in EP-A-0,203,838, hereby expressly incorporated by reference.

Moreover, by the term "doped" sesquisulfides are intended rare earth metal sesquisulfides as described above, but additionally containing one or a plurality of alkali metals, one or a plurality of alkaline earth metals, or else, alternatively, mixtures of alkali metal(s) and alkaline earth metal(s), such alkali/alkaline earth elements being situated, at least in part, occluded in the crystal lattice of said sesquisulfides. The expression "doping element" or "dopant" will hereinafter be used, for the sake of simplicity, to represent both an alkali metal and an alkaline earth metal, it being appreciated that this term also encompasses any combination of alkali metal(s) and/or alkaline earth metal(s), as indicated above. Such doped sesquisulfides and a process for the preparation thereof are described in FR-91/14,988, also expressly incorporated by reference. A detailed description of these products and a process for the preparation thereof will follow.

Briefly, the present invention features novel colored inorganic pigments based on rare/earth metal sesquisulfides having improved properties, especially enhanced chromatic properties, said novel pigments, preferably those that have been doped, having been subjected to a fluoridation treatment.

DETAILED DESCRIPTION OF BEST MODE AND PREFERRED EMBODIMENTS OF THE INVENTION

More particularly according to the present invention, by the term "fluoridation treatment" is intended, in general, any treatment capable of introducing and of fixing fluorine atoms in the, and preferably at the surface of the starting material sesquisulfides.

Without wishing to be bound to or by any particular theory, it is believed that the fluoridation treatment according to the invention provides a more or less pronounced modification in the initial surface state of the treated pigments, which modification is thought to be the reason for the improvement in certain of the properties thereof, especially their coloration. This modification can, in particular, be revealed by Auger, ESCA and X-ray diffraction analyses of the treated products, or the products over the course of treatment.

The pigments produced by the above fluoridation treatment constitute a primary aspect of the present invention.

These novel pigments based on rare earth metal sesquisulfides are thus essentially characterized in that they contain fluorine atoms.

Moreover, the subject fluoridated pigments preferably have at least one of the following characteristics:

(a) the fluorine atoms are distributed along a concentration gradient decreasing from the surface to the core of said sesquisulfides, (b) the fluorine atoms are primarily distributed at the outer periphery of said sesquisulfides (by the term "outer periphery" is intended a thickness of material, measured from the surface of the particle, on the order of a few hundreds of angstroms; moreover, by the term "primarily" is intended that more than 50% of the fluorine atoms present in the sesquisulfide are located at said outer periphery), (c) the percentage by weight of fluorine atoms present in the sesquisulfide does not exceed 10%, and preferably does not exceed 5%, and (d) the fluorine atoms are present in the form of fluoro or sulfofluoro compounds, in particular in the form of rare earth metal fluorides or rare earth metal sulfofluorides (thiofluorides).

In a preferred embodiment of the present invention, the fluoridated pigments resulting from the fluoridation stage can additionally subsequently be encapsulated by transparent oxides to provide composite particles of core/shell type via a technique such as described in the aforenoted FR-93/04,544, also incorporated by reference. A detailed description of this encapsulation process, and the resulting products, will follow. The fluorinated pigments thus encapsulated have, with respect to the corresponding non-encapsulated products, improved chemical stability and improved thermal stability, and, indeed, in certain instances, an improved coloration.

The process according to the invention thus comprises contacting/reacting a rare earth metal sesquisulfide with a fluoridating agent.

The fluoridation can be carried out via any technique.

In particular, the fluoridating agent can be liquid, solid or gaseous. The reaction is preferably carried out under conditions such that the fluoridating agent is liquid or gaseous.

Particularly exemplary fluoridating agents well suited for carrying out the present invention include fluorine $F_2$, halogen fluorides, ammonium fluoride, rare gas fluorides, nitrogen trifluoride $NF_3$, boron trifluoride $BF_3$, tetrafluoromethane or hydrofluoric acid HF.

In the instance of treatment under a fluoridating atmosphere, the fluoridating agent can be employed pure, or diluted in a neutral or inert gas, for example nitrogen.

The pigments to be treated are, preferably, initially in the form of a finely divided and homogeneous powder, such as to facilitate the fluoridation thereof. It will be appreciated that the process according to the invention presents the added advantage, inter alia, of not, or only slightly, disturbing or disrupting the particle size of the constituent particles of the starting pigment.

The reaction conditions are preferably selected such that the treatment only effects fluoridation at the surface of the material (gentle conditions). In this respect, extending the fluoridation deep into the core of the starting material does not produce substantially improved results vis-a-vis an essentially surface fluoridation. In actual practice, it is possible to experimentally monitor and control the degree of progress of the fluoridation reaction, for example by measuring the change in the uptake in mass or increase in weight of the materials (caused by progressive introduction of fluorine values).

Various specific methods, and the reaction conditions pertaining thereto, as regards actually carrying out the fluoridation processes of the invention will be more fully described below. Of course, the present invention is not restricted to these various specific examples, but also encompasses all possible variations thereof. In particular, modifications to certain experimental parameters such as pressure, temperature, dilution and nature of the fluoridating agent; duration and rate (dynamic or static) of the fluoridation; and the like, which permit optimization of the coloration of the pigments based on rare earth metal sesquisulfides, can be made without departing from the scope of this invention.

It will be appreciated that the treatment according to the invention is of general application and scope, namely, it is suitable for the treatment and preparation of the entire range of different rare earth metal sesquisulfides, to significantly improve the coloring properties thereof. Of course, the starting pigment based on rare earth metal sesquisulfides determines and conditions the final coloration of the corresponding fluoridated pigment in accordance with the invention. Stated differently, obtaining a fluoridated pigment which must have a given final color naturally entails use of a starting pigment which originally has the same color. Thus, the treatment according to the invention does not substantially modify the nature and the chemical composition, on the one hand, and the basic intrinsic color, on the other, of the original pigment. It thus transpires that the pigments according to the invention are only distinguished from the starting material pigments (before treatment) essentially by the presence of the fluorine atoms, on the one hand, and an improved coloration on the other. Too, it will be appreciated that the treatment according to the invention presents another major advantage in not modifying or disturbing the other original basic pigment properties of the starting materials, namely, principally their coloring power, their opacifying power and their dispersibility in the materials or substrates to be colored.

The starting material pigments of the present invention will now be more fully described.

Thus, the process according to the invention is particularly well suited for the treatment and production of pigments based on rare earth metal sesquisulfides of doped type (presence of one or more alkali metal and/or alkaline earth metal elements in the crystal lattice of the sesquisulfide), such as described in FR-91/14,988, and which already intrinsically possess many advantageous properties, especially a markedly improved coloration vis-a-vis the corresponding undoped pigments. The process according to the invention is nevertheless also suitable for the treatment of undoped sesquisulfides, especially those described in EP-A-0,203,838.

The doping element can be present in the pigment in various forms. However, in a preferred embodiment of the invention, it is essentially present in a form combined with the rare earth metal sesquisulfides. In this event, the doping element is then irreversibly bonded to the sesquisulfides, in the sense that, for example, even very thorough washing of the latter does not remove the dopant. Such washing, to the contrary, can remove the alkali metal or alkaline earth metal sulfide(s) and/or polysulfide(s) optionally present at the surface of the pigments (before fluoridation) and thus not irreversibly bonded thereto.

Again without wishing to be bound to or by any particular theory regarding the causes and effects of the doping, it is known that rare earth metal sesquisulfides $M_2S_3$ crystallize in a crystallographic structure of $Th_3P_4$ type, which has gaps in the cation lattice; this lacunary structure can be symbolized by giving the sesquisulfides the formula $M_{10.66}[\ ]_{1.33}S_{16}$ (in this respect see, in particular, W. H. Zachariasen, "Crystal Chemical Studies of the 5f-Series of Elements. The $Ce_2S_3$—$Ce_3S_4$ Type of Structure", *Acta Cryst.*, 2, 57 (1949)).

Thus, it has now been found that alkali metal and/or alkaline earth metal elements can be introduced into these cationic gaps, optionally up to the saturation thereof. The presence of the doping element within the pigments obtained or used in the invention can thus be demonstrated by simple chemical analysis. Moreover, X-ray diffraction analyses evidence that the $Th_3P_4$ crystal phase of the sesquisulfide is retained with, in certain instances, modification of the lattice constants to a greater or lesser extent, depending both on the nature and the amount of the dopant introduced.

Completely unexpectedly and surprisingly, it transpires that this insertion within the crystal lattice of the sesquisulfide imparts thereto chromatic characteristics which are markedly improved with respect to all known rare earth metal sesquisulfides (undoped). Moreover, the presence of such doping element can provide the beneficial effect of stabilizing the crystal structure of the sesquisulfide under consideration at high temperatures and, thus, of preserving the desired coloration over a wider temperature range.

In a preferred embodiment of the fluoridated pigments according to the invention, the doping element present in the sesquisulfide is an alkali metal element selected, for example, whether alone or in admixture, from among lithium, sodium and potassium. More preferably, the alkali metal is sodium.

Particularly exemplary alkaline earth metal elements according to the invention are magnesium, calcium, barium and strontium.

In another preferred embodiment of said pigments, the molar amount of alkali metal(s) and/or alkaline earth metal(s) present in the pigment is at least equal to 0.1%, and advantageously ranges from 5% to 50%, of the molar amount of the rare earth metal(s) present therein.

As indicated above, the nature of the rare earth metal(s), and of the crystal lattice type of the sesquisulfide, are selected according to the color desired for the pigment after fluoridation. Moreover, in all instances, it is observed that, for a suitably selected doping element, the fluoridated pigments according to the invention then have much more intense colorations than those of the corresponding sesquisulfides not doped with an alkali metal and/or alkaline earth metal element; by the term "corresponding sesquisulfide" is intended the sesquisulfide containing the same rare earth metal(s) and having the same crystallographic habit.

For a given rare earth metal sesquisulfide, and thus a given coloration, it is thus possible to provide, after simple routine tests, an entire range of pigments of improved colors, simply by adjusting the nature and/or the concentration of a doping element in the pigment.

Examples of colors which can be obtained with the fluoridated pigments according to the invention are given below, according to the nature of the original pigment (doped or undoped), these being given purely by way of illustration and without limitation:

(i) treated pigments which are based on cerium sulfides have a color varying from brown to red depending on the preparation conditions, in particular the calcination temperature. They are brown or blood-red depending on whether the β-orthorhombic $Ce_2S_3$ phase (J.C.P.D.S. 20 269) or the γ-cubic $Ce_2S_3$ phase (J.C.P.D.S. 27 104) is present, (ii) with lanthanum, yellow pigments are obtained having a cubic $La_2S_3$ structure (J.C.P.D.S. 25 1041), (iii) a green coloration can be obtained with neodymium and a yellow-green coloration with praseodymium; the pigments then respectively have the cubic $Nd_3S_3$ structure (J.C.P.D.S. 26 1450) and the cubic $Pr_2S_3$ structure (J.C.P.D.S. 27 481), (iv) a brown-yellow pigment is available with dysprosium of cubic $Dy_2S_3$ structure (J.C.P.D.S. 26 594), (v) pigments having various shades of brown can also be obtained; ochre with terbium of cubic $Tb_2S_3$ structure, brown with erbium of monoclinic $Er_2S_3$ structure (J.C.P.D.S. 21 324) and dark beige with yttrium of monoclinic $Y_2S_3$ structure (J.C.P.D.S. 22 996), (vi) finally, other examples of colors which can be obtained are: grey-brown with samarium of cubic $Sm_2S_3$ structure (J.C.P.D.S. 26 1480), green-brown with gadolinium of γ-cubic $Gd_2S_3$ structure (J.C.P.D.S. 26 1424) or gold-green with thullium of monoclinic $Tm_2S_3$ structure (J.C.P.D.S. 30 1364).

The intrinsic coloration of the starting doped pigments and of the fluoridated doped pigments according to the invention can moreover be quantified by means of the chromatic coordinates L*, a* and b* reported in the CIE system 1976 (L*, a*, b*) as defined by the International Lighting Commission and cataloged in the Compilation of French Standards (AFNOR), colorimetric color No. X08-12 (1983). These are determined using a colorimeter marketed by Pacific Scientific. The illuminant is of D65 type. The surface observed is a circular pellet having a surface area of 12.5 cm $^2$. The observation conditions correspond to viewing with an aperture angle of 10°. The specular component is excluded from the measurements.

L* provides a measure of the reflectance (light/dark shading) and thus varies from 100 (white) to 0 (black).

a* and b* are the values of the color trends:
a* positive =red
a* negative =green
b* positive =yellow
b* negative =blue L* thus represents the variation from black to white, a* the variation from green to red and b* the variation from blue to yellow.

Thus, according to the present invention and solely by way of example, when the rare earth metal is cerium and the sesquisulfide is in its γ-cubic crystallographic form, pigments are available which have the following exceptional trichromatic coordinates:

L* at least equal to 30 and in particular ranging from 30 to 60, a* at least equal to 30 and in particular ranging from 35 to 65, b* generally ranges from 0 to 55.

Such coordinates, and in particular the a* chromatic coordinate, correspond to an intense red color completely exceptional for a γ-cubic cerium sulfide $Ce_2S_3$ and is equivalent to or indeed better than that of the reference red pigments, namely, cadmium selenide and cadmium sulfoselenide. Moreover, one of the advantages of such a pigment is that it does not present the toxicity problems associated with the presence of heavy metals, as is generally the case with the pigments of the prior art.

As will clearly be seen from the specific examples presented below, the fluoridation treatment according to the invention is particularly well suited for substantially and significantly improving the a* chromatic coordinate (red trend) of pigments based on γ-cubic cerium sesquisulfide $Ce_2S_3$ doped with sodium.

A particularly advantageous industrial process suitable for the synthesis of sesquisulfides doped with alkali metals and/or alkaline earth metals such as described above, the latter products constituting one of the preferred starting materials for the preparation of the fluoridated pigments according to the invention, will now follow. It will be appreciated that the process which follows, which moreover is the subject of FR-91/14,988, is particularly well suited, inter alia, for obtaining compositions in which the rare earth metal sesquisulfide exists in a cubic, and in particular γ-cubic, crystalline form.

This process entails producing a starting mixture containing at least one rare earth metal compound, sulfur and at least one compound of an alkali metal and/or alkaline earth metal element (doping element), heating such starting mixture, under a non-oxidizing and preferably reducing atmosphere, until the desired sesquisulfide phase is attained, and then cooling the mixture thus treated.

In a preferred embodiment of this process, heating of the starting mixture is carried out in the presence of a reducing agent. The amount of reducing agent added is then determined such as to maintain a very low oxygen partial pressure in the reactor. Thus, the amount of reducing agent used is advantageously sufficient to consume the free and/or combined oxygen contained in the starting mixture.

In a first variant of this embodiment, a reducing agent is added directly to the starting mixture. This agent is generally carbon-based, such as, for example, graphite, coke or lignite or, alternatively, an organic compound which generates carbon on heating. Same can also be a metal reducing agent, for example aluminum.

According to a second variant of this embodiment, the reducing agent is contained in the gas constituting the non-oxidizing atmosphere. The starting mixture is then advantageously swept with a non-oxidizing gas, preferably an inert gas, containing a reducing agent such as, for example, hydrogen or carbon monoxide CO. Thus, a mixture of hydrogen with an inert gas can be used, such as an argon/hydrogen or nitrogen/hydrogen mixture, or else, alternatively, an argon/CO or nitrogen/CO mixture. This sweeping can also be carried out using hydrogen or carbon monoxide alone.

Advantageously, during the increase in temperature, the mixture is maintained at an intermediate temperature, in particular ranging from 250° C. to 500° C. before adjusting it to the temperature corresponding to the formation of the desired sesquisulfide. This holding at an intermediate temperature is carried out for a period of time generally ranging from 15 minutes to 1 hour.

Rare earth metal compounds which are suitable for carrying out the above process are, for example, selected from among oxygen- and carbon-containing rare earth metal compounds, rare earth metal sulfates or rare earth metal oxides. Exemplary oxygen- and carbon-containing rare earth metal compounds include, in particular, rare earth metal carbonates, oxalates, acetates, malonates or tartrates.

Representative alkali metal or alkaline earth metal compounds include, for example, alkali metal or alkaline earth metal oxides, sulfides or polysulfides, sulfates or oxygen- and carbon-containing compounds such as oxalates, carbonates or acetates. Preferably, carbonates of these elements are used.

The amount of alkali metal or alkaline earth metal element added is determined such as to provide a doping element/rare earth metal(s) molar ratio generally ranging from 0.05 to 0.5 and preferably from 0.15 to 0.30 in the starting mixture.

Moreover, the amount of sulfur present in the starting mixture is determined such as to provide a sulfur/rare earth metal(s) molar ratio greater than or equal to 1.5 and preferably greater than 2.

The sulfur can be introduced in the free state (solid or gaseous elemental sulfur) or in the form of a sulfur-containing precursor compound, for example $Na_2S$, $H_2S$ or $CS_2$.

Preferably, either elemental sulfur in the solid state or gaseous $CS_2$ is used.

The starting mixture can, of course, comprise a plurality of the above rare earth metal and/or alkali metal and/or alkaline earth metal compounds.

The starting mixture thus obtained is then heated at a temperature and for a period of time sufficient to produce the desired sesquisulfide phase, this time period generally being shorter as the temperature increases. This temperature depends, of course, on the sesquisulfide under consideration.

Advantageously, the mixture is heated at a temperature greater than 900° C., generally ranging from 1,000° to 1,400° C. and preferably from 1,150° to 1,300° C., for at least 30 minutes and preferably from 30 minutes to 2 hours.

The product thus obtained can then optionally be subjected to one or more washings, for example with water, to reduce the content of unbonded alkali metal(s) and/or alkaline earth metal(s).

If necessary, the product obtained can lastly be ground (air jet milling or otherwise) to provide a mean particle diameter of from 0.2 μm to 5 μm. However, according to the process as described above, this particle size is generally obtained without having to grind the product, which constitutes a very significant advantage from an economic standpoint.

The final product then has a very good phase purity (in particular absence of oxysulfide) and remarkably high chromatic coordinates in the specific color of the rare earth metal sesquisulfide under consideration.

As indicated above, these products (doped rare earth metal sesquisulfides) are then used as one of the starting materials which are treated in accordance with the process of the present invention, to produce the subject fluoridated pigments which have improved, especially chromatic, properties.

As indicated above, the novel fluoridated pigments according to the invention are advantageously encapsulated, via a technique such as described in FR-93-04,544 with a layer of transparent oxides, to provide fluoridated pigments having, with respect to the corresponding non-encapsulated fluoridated products, an improved chemical stability and an improved thermal stability, and, indeed, in certain cases, an improved coloration as well.

According to this encapsulation technique, more fully described below, novel colored composite pigments of core/shell type are thus obtained, comprising:

(A) a substrate (or core or nucleus) based on at least one fluoridated rare earth metal sesquisulfide (Whether doped or nondoped) as described above, and (B) a layer (or shell, sheath or envelope) based on at least one transparent oxide, deposited onto the surface of the substrate and coating same.

Of course, certain variants of this structure are possible. In particular, the peripheral or outer layer coating the particle need not be perfectly continuous or homogeneous. However, preferably, the pigments according to the invention comprise a transparent oxide coating layer which is uniform and of controlled thickness, such as not to detrimentally affect the original color of the substrate before coating.

By the term "transparent oxide" is intended an oxide which, once deposited onto a substrate in the form of a more or less thin film, does not absorb or only very slightly absorbs light rays in the visible range, such as not to, or to only very slightly mask, the intrinsic original color of the substrate. Moreover, it will also be appreciated that the term oxide, which is used simply for convenience, includes the oxides of hydrated type.

These oxides, or hydrated oxides, can be amorphous and/or crystalline.

Particularly exemplary of such oxides are silicon oxide (silica), aluminum oxide (alumina), zirconium oxide (zirconia), titanium dioxide, zirconium silicate $ZrSiO_4$ (zircon) and rare earth metal oxides. Among the latter, it is preferable to use those which do not exhibit officially recognized toxicity to man and/or the environment.

In a preferred embodiment of the composite pigments of the present invention, the coating layer is based on silica. More preferably, this layer consists essentially of silica, and, even more preferably, is completely silica.

The novel composite pigments described above can be used as colored pigments due to their many and multiple advantageous properties, such as, especially a very wide range of excellent intrinsic coloration, a very good coloring power, a very good opacifying power, a very good dispersibility, especially in plastics, a very good thermal stability at temperatures which can range up to 500° C. and a good chemical stability in media such as water (at neutral, basic or slightly acidic pH) and organic solvents.

The synthesis (encapsulation) of the composite pigments according to the invention will now be more fully described. This process comprises the following essential stages:

(i) contacting an inorganic substrate as described above with a precursor of the desired transparent oxide, (ii) precipitating the transparent oxide, and (iii) separating the composite pigment obtained from the reaction medium.

Overall, such a process is based on the principle of a chemical precipitation of a transparent oxide precursor carried out "in situ" in a medium comprising a dispersion (or suspension) of the aforesaid inorganic substrate, the precipitated oxide then being deposited onto the surface of each of the particles of the inorganic substrate. Thus produced, directly in the reaction medium, are composite particles (or pigments) which correspond to the starting fluoridated substrate, but in a form perfectly encapsulated by an external transparent oxide protective layer of controlled thickness.

This encapsulation process presents the advantage, inter alia, of not, or only slightly, disturbing, on the one hand, the particle size of the particles constituting the starting substrate before coating and, on the other, the excellent intrinsic chromatic characteristics thereof. It is even possible for said characteristics to be substantially improved thereby; additionally, the shell thus constituted at the surface of the starting particles makes it possible to produce pigments in which the thermal and chemical stability properties are markedly improved.

The precipitation techniques which can be used in the encapsulation process are manifold and generally vary with the nature of the desired transparent oxide. It should be appreciated that there exists one common general requirement to be observed to properly carry out all of these precipitation processes, namely, it is advisable, to the extent possible, to prevent the fluoridated rare earth metal sesquisulfides employed as the substrate from coming into contact, before or during the precipitation stage, with an excessively acidic medium which could cause decomposition thereof.

The encapsulation will first be described in the specific and preferred embodiment where the layer-forming oxide is silica.

This encapsulation with silica can be carried out essentially according to two embodiments.

In the first embodiment, which is preferred to the second, described below, the silica is prepared by hydrolysis of an alkyl silicate.

More particularly, the substrate and an alkyl silicate are intimately contacted, the alkyl silicate being hydrolyzed, and the pigment formed and the liquid phase of the reaction medium are then separated.

The principle of this technique is more particularly described in Stöber et al, *Journal of Colloid and Interface Science*, 26, pp. 62–69 (1968), hereby incorporated by reference.

Generally, it is preferable to carry out the hydrolysis in the presence of a base, which then serves as a catalyst.

The reaction is carried out by forming a reaction medium by mixing water, alcohol, the substrate, which is then suspended, and, optionally, a base, and by then introducing the alkyl silicate. The reaction is preferably carried out with stirring.

It is possible to use ammonia as the base. The alcohols used are generally aliphatic alcohols, such as, for example, butanol. The alkyl silicate is preferably introduced with an alcohol.

Although the reaction can be carried out at room temperature, a substantial improvement in the quality of the coating layer is attained, however, when the hydrolysis temperature is greater than room temperature, in particular ranging from 40° C. to 70° C.

It is also possible to prepare vessel bottoms based on alcohol and alkyl silicate and to then introduce therein the water or a water-based mixture.

Ethyl silicate, in particular, can be employed as the alkyl silicate.

After reaction and precipitation, the pigment obtained is separated from the reaction medium by any technique per se known to this art, in particular by centrifuging or by filtration, and is then generally washed with alcohol and then finally dried.

As regards the second embodiment, the process entails contacting, intimately admixing and reacting the substrate, a silicate and an acid, by which silica is precipitated.

In a first variant of this second embodiment, the acid and the silicate are added simultaneously to the reaction medium. More particularly, an aqueous suspension of the substrate is first formed and then the acid and an aqueous silicate solution are added simultaneously to the reaction medium.

According to a specific technique, the acid and the silicate can then be introduced while maintaining the pH of the reaction medium constant. Generally, this pH is maintained at a value of from 8 to 9.

The reaction temperature can vary widely. In general, this temperature ranges from 60° to 100° C.

A second variant (preferred to the first) of this second embodiment of the process according to the invention comprises first forming a suspension of the substrate in an aqueous silicate solution and then introducing the acid into the suspension thus formed. In this case, the pH of the precipitation medium is advantageously established at a value greater than 7, and preferably greater than 8, such as to prevent harmful dissolution of the substrate based on rare earth metal sulfides.

In this second variant, the temperature conditions are identical to those described in the first.

As regards the silicate, an alkali metal silicate, and more particularly a sodium, potassium or lithium silicate, is generally used.

With respect to the acids, sulfuric, nitric or hydrochloric acids, or carbon dioxides are generally used. The acid is typically employed in the form of an aqueous solution thereof.

Separation between the pigment, on the one hand, and the liquid phase of the reaction medium, on the other, is then carried out in a manner per se known to this art, for example by filtration. The separated pigment is then dried.

In the event that the layer-forming oxide is alumina, a number of embodiments are also possible.

According to a first embodiment, the substrate, an aluminate and an acid are contacted and reacted, by which alumina precipitates.

In a first variant of this first embodiment, the aluminate and the acid can be introduced simultaneously into an aqueous suspension of the substrate. In this instance, it is possible to carry out the reaction such as to maintain the pH of the reaction medium constant, this pH preferably being greater than 7 and still more preferably greater than 8.

In a second variant of this first embodiment, a suspension of the substrate in an aluminate solution is first formed and then the acid is introduced into this suspension. Again, care should be taken that the pH of the reaction mixture during introduction of the acid preferably remains greater than 7 or even greater than 8.

An alkali metal aluminate is generally used in this first embodiment. The acid, in turn, can be, for example, hydrochloric acid or nitric acid.

The second embodiment for the preparation of a composite pigment according to the invention with alumina as the layer-forming oxide entails contacting, intimately admixing, and reacting the substrate, an aluminum salt and a base, by which alumina precipitates.

Thus, for example, an aqueous suspension of the substrate can be introduced into suitable vessel and then the base and the aluminum salt can be simultaneously added to this suspension.

The base is generally sodium hydroxide or ammonia and the aluminum salt can be, for example, an aluminum halide such as aluminum chloride or, alternatively, aluminum nitrate.

Finally, in a third embodiment, the composite pigments can be prepared from an alumina obtained by hydrolysis of an aluminum alkoxide.

This embodiment is similar to that described above for hydrolysis of an alkyl silicate.

The reaction is then carried out by bringing together the substrate and an aluminum alkoxide, this alkoxide being hydrolyzed and the pigment formed and the liquid phase of the reaction medium are separated.

That described above in respect of the hydrolysis of an alkyl silicate applies here as well, especially as regards the use of a base and the method of introduction of the reactants.

Exemplary aluminum alkoxides include aluminum methoxide, ethoxide, isopropoxide or butoxide, these alkoxides being in the liquid state, or in the solid state as a dispersion or as a solution in an organic solvent, for example benzene or the corresponding alcohol.

In the event of preparation of a composite pigment comprising titanium dioxide as the layer-forming oxide, various preparative techniques are possible.

The first comprises precipitating $TiO_2$ by introducing a titanium salt, on the one hand, such as $TiCl_4$, $TiOCl_2$ or $TiOSO_4$, and a base, on the other, such as sodium hydroxide or ammonia, into an aqueous suspension of the substrate, introduction of the salt and of the base being carried out simultaneously. It is then possible to effect a curing of the pigment.

A second technique comprises hydrolyzing an alkyl titanate, for example isopropyl titanate. This method is of the same type as that described above for the hydrolysis of an alkyl silicate. The reaction is thus carried out by bringing together the substrate and an alkyl titanate, the alkyl titanate is then hydrolyzed and the pigment formed and the liquid phase of the medium are separated. That described above as regards the introduction of the reactants is also here applicable.

For the preparation of composite pigments comprising zirconium oxide as the layer-forming oxide, the preparative techniques are of the same type as those described above for titanium dioxide, namely, precipitation by reaction between a zirconium salt and a base, or hydrolysis of an alkyl zirconate.

Likewise, for the preparation of composite pigments comprising one or more rare earth metal oxides as layer-forming oxides, the reaction can be carried out either by hydrolysis of a rare earth metal alkoxide, or by precipitation by simultaneously introducing, on the one hand, a rare earth metal salt (nitrate or chloride) and, on the other, a base (sodium hydroxide or ammonia, for example) into an aqueous suspension of the substrate.

Finally, in the case of zircon defining a layer around the substrate, the preparation can be carried out in the following manner: a zirconium alkoxide, on the one hand, and a silicon alkoxide, on the other, are cohydrolyzed in an aqueous suspension of the substrate in the presence of sodium fluoride NaF. The pigment thus formed is recovered and then calcined to convert the precipitated coating layer into a zircon phase. The NaF then serves as a flux to assist the conversion at the lowest possible temperature.

It is also within the scope of the present invention to prepare pigments having either a plurality of oxides forming a plurality of successive layers, or mixtures of oxides or mixed oxides forming the same layer.

Additionally, one or more pretreatments of the substrate (before coating) can be carried out to further improve certain of its characteristics or properties during the coating treatment, or even of improving some of the characteristics or properties of the resulting composite pigment.

The particle size of the composite pigments recovered is fine and even and advantageously ranges from 1 to 5 microns. With such a particle size, the products can be directly used as pigments, especially for plastics. As indicated above, this particle size is directly related to the starting particle size of the substrate particles employed in the coating process. The starting particle size must thus be selected according to and in anticipation of the particle size desired for the final composite pigment and with a view to a specific given application.

In addition to their excellent intrinsic colors (encapsulated or non-encapsulated fluoridated pigments) and their improved chemical and/or thermal stability (encapsulated fluoridated pigments), the pigments according to the invention have a very good coloring power and a very good opacifying power and, for this reason, are perfectly suited for the coloration of many materials, such as plastics, paints and others. In this respect, the polyvalency of the pigments according to the invention presents one of their great advantages.

Thus, particularly, the pigments of the invention are well suited for the coloration of plastics, whether of thermoplastic or thermosetting type.

Exemplary thermoplastic resins suited for coloration according to the invention include poly(vinyl chloride), poly(vinyl alcohol), polystyrene, styrene/butadiene, styrene/acrylonitrile or acrylonitrile/butadiene/styrene (A.B.S.) copolymers, acrylic polymers, in particular poly(methyl methacrylate), polyolefins such as polyethylene, polypropylene, polybutene or polymethylpentene, cellulose derivatives such as, for example, cellulose acetate, cellulose acetobutyrate or ethyl cellulose, or polyamides including nylon 66.

Exemplary thermosetting resins well suited for coloration according to the invention include the phenoplasts, aminoplasts, in particular urea/formaldehyde or melamine/formaldehyde copolymers, epoxy resins and thermosetting polyesters.

The pigments of the invention can also be formulated into specialty polymers such as fluoridated polymers, in particular polytetrafluoroethylene (P.T.F.E.), polycarbonates, silicone elastomers or polyimides.

In this specific application for the coloration of plastics, the pigments of the invention can be directly used in the form of powders. It is preferred, however, to use them in a predispersed form, for example as a premix with a portion of the resin, in the form of a pasty concentrate or of a liquid, which permits the introduction of same at any stage in the manufacture of the resin. This is a particularly significant advantage of the pigments of the invention.

Thus, the pigments of this invention can be incorporated into plastics such as those indicated above in a proportion by weight generally ranging either from 0.01% to 5% (relative to the final product), or from 40% to 70% in the case of a concentrate.

The pigments of the invention can also be used in the field of paints and varnishes and, more particularly, can be formulated with the following resins: alkyd resins, the most common of which is known as glycerophthalic; resins modified with tall or short oil; acrylic resins prepared from esters of acrylic (methyl or ethyl) and methacrylic acid optionally copolymerized with ethyl, 2-ethylhexyl or butyl acrylate; vinyl resins such as, for example, poly(vinyl acetate), poly(vinyl chloride), poly(vinyl butyral), poly(vinyl formal) and vinyl chloride and vinyl acetate or vinylidene chloride copolymers; aminoplastic or phenolic resins, typically modified; polyester resins; polyurethane resins; epoxy resins; or silicone resins.

Typically, the pigments are incorporated in a proportion of 5% to 30% by weight of the paint and of 0.1% to 5% by weight of the varnish.

Lastly, the pigments according to the invention are also suitable for applications in the rubber industry, especially in floor coverings in the paper and printing inks industry, in the field of cosmetics and for many other applications such as, for example, and without limitation, leather finishing and laminated coatings for kitchens and other cooking surfaces, or ceramics.

More particularly as regards cosmetics, the pigments of the invention can be included in nail varnishes and polishes and in make-up such as lipsticks, powder make-up preparations, cream make-up preparations, or foundation creams.

They can thus be formulated into nail varnishes and polishes which generally contain:

(a) a film-forming agent based on nitrocellulose,
(b) a resin, natural dammar resin or synthetic resin of formaldehyde/sulfamide type, polystyrene resin, polyvinyl resin, and the like,
(c) a plasticizer, for example diethyl phthalate, dibutyl phthalate, dioctyl phthalate, tricresyl phosphate, n-butyl stearate, resorcin diacetate, or mixture thereof,
(d) a solvent such as ethyl, isopropyl, butyl or isobutyl alcohol, ethyl acetate, butyl acetate or, most often, a mixture of these solvents,
(e) a diluent, especially toluene or xylene,
(f) optionally, other additives, fragrance or pearlescent material (mica flakes coated with bismuth oxychloride or titanium dioxide).

One example of a typical such composition is given below:

(i) from 10% to 15% by weight of nitrocellulose,
(ii) from 10% to 15% by weight of resin,
(iii) from 3% to 5% by weight of plasticizer(s),
(iv) from 3% to 5% by weight of pigment(s),
(v) q.s. for 100% by weight of solvent(s).

Generally, the pigments are ground in a plastic mass comprising nitrocellulose and plasticizer(s), which is then dissolved in the solvent(s).

Another application of the pigments of the invention is for lipsticks.

The pigments are typically included in the proportion of a concentration by weight of 5% to 15%, expressed with respect to the total weight of the formulation which contains:

(a') an excipient formed from a mixture of various materials to provide for the consistency: beeswax, carnauba wax, ozocerites, paraffin wax, synthetic waxes or mixture thereof and of a soft excipient which permits adjusting the consistency, such as cocoa butter, petroleum jelly or hydrogenated white oils, for example palm, groundnut or castor oil, (b') various additives, in particular a fragrance, perfume or aroma and isopropyl myristate or isopropyl palmitate which provides a slippery or wet appearance, (c') an intermediate solvent for suspending the pigment in the lipophilic phase which can be castor oil or a glycol such as polyoxyethylene glycol 400, or fatty acid esters such as propylene glycol monoricinoleate, isopropyl myristate, isopropyl palmitate or butyl stearate.

The eyeshadows and blushes can exist in the form of powder make-up preparations or of cream make-up preparations. The pigment content in such make-up preparations can vary over wide limits, e.g., from 5% to 20%.

Powder make-up preparations are powders (talc, magnesium carbonate, zinc stearate) which are filled with pigments and agglomerated either with methyl cellulose or with stearates.

| One composition of an eyeshadow is as follows: | | |
|---|---|---|
| (i) | aluminum magnesium silicate (Veegum F): | 7% by weight |
| (ii) | talc: | 50% by weight |
| (iii) | zinc oxide: | 4% by weight |
| (iv) | zinc stearate: | 11% by weight |
| (v) | kaolin: | 10% by weight |
| (vi) | pigment: | 18% by weight |

The pigments of the invention can also be incorporated into foundation cream formulations.

The foundation creams are provided in the form of an emulsion, generally of oil-in-water type.

The lipophilic phase most often comprises:

(a") an oily component such as liquid paraffin, esters of fatty acids and, optionally of fatty alcohols, for example oleyl oleate, decyl oleate, octyl stearate, di-n-butyl adipate, isopropyl myristate, isopropyl palmitate, isopropyl stearate, esters of capric and caprylic acids with saturated fatty alcohols having from 12 to 18 carbon atoms, a silicone oil, or mixtures of the above, (b") an emulsifying agent of anionic and/or non-ionic type and, more particularly, fatty acid salts, sodium, potassium or ammonium stearate or sodium palmitate; esters of sorbitan and of fatty acids such as, for example, lauric acid, palmitic acid or stearic acid; polyoxyethylenated esters of sorbitan and of fatty acids having from 4 to 20 mol of ethylene oxide per mole of ester; polyoxyethylenated fatty alcohols having from 2 to 23 mol of ethylene oxide per mole of alcohol, the alcohol, in particular, being lauric alcohol, cetyl alcohol, stearyl alcohol or oleyl alcohol; glycerol mono- and distearate or glycerol mono- and dioleate; polyoxyethylenated fatty acids and, in particular, polyoxyethylenated stearate having from 18 to 100 mol of ethylene oxide per mole of acid, (c") an agent which permits adjusting consistency, for example a fatty alcohol or a fatty acid and, more particularly cetyl alcohol, stearyl alcohol or stearic acid.

With respect to the hydrophilic phase, it comprises water, preferably distilled, and various additives, in particular:

(a'") a humectant which can be, for example, propylene glycol, glycerol or sorbitol, (b'") a preserving agent or preservative and, more particularly, o-phenylphenol and the following acids, their salts (Na, K, $NH_4$) or their esters having from 1 to 4 carbon atoms: benzoic acid, salicylic acid, sorbic acid or p-hydroxybenzoic acid, (e'") a stabilizing agent, in particular cellulose derivatives including carboxymethylcellulose and xanthan gum.

One illustration of a formulation for a foundation cream is given below:

| (1) Lipophilic phase: | | |
|---|---|---|
| (i) | liquid paraffin: | 15% by weight |
| (ii) | glycerol mono- and distearate: | 4% by weight |
| (iii) | cetyl alcohol | 1% by weight |
| (2) Hydrophilic phase: | | |
| (i) | distilled water q.s. for: | 100% by weight |
| (ii) | propylene glycol: | 3% by weight |
| (iii) | methyl para-hydroxybenzoate: | 0.05% by weight |
| (iv) | propyl para-hydroxy benzoate: | 0.1% by weight |
| (3) Colored pigment: | | 1 to 10% by weight |
| (4) Titanium dioxide: | | 3% by weight |

The preparation of the foundation cream formulations is carried out by first dispersing the pigment in the lipophilic phase maintained at about 60°–80° C. and then the hydrophilic phase, maintained at one of the temperatures in the above range, is added slowly and with stirring to the lipophilic phase.

In the aforesaid description, examples of formulations intended for cosmetics are set forth in which the pigments of the invention are suitable; these, of course, are for purposes of illustration only.

In order to further illustrate the present invention and the advantages thereof, the following specific examples are given, it being understood that same are intended only as illustrative and in nowise limitative.

EXAMPLE 1

A γ-cubic cerium sesquisulfide $Ce_2S_3$ doped with sodium was prepared as described in FR-91/14,988, i.e., a mixture of cerium oxalate, anhydrous sodium carbonate and elemental sulfur, was placed in a consumable carbon graphite boat, the starting Na/Ce molar ratio in the mixture having been set at 0.2, and calcined at 1,050° C. in an airtight tubular furnace which had been purged beforehand and which was continuously swept with argon laden with 10% hydrogen.

The product recovered after calcination was then washed once with deionized water.

The product obtained then had a very intense red color. X-ray diffraction analysis indicated that the single γ-cubic $Ce_2S_3$ phase had been obtained, having a lattice constant equal to 8.637 Å. The sodium content of the product was 2.25% by weight (Na/$Ce_2S_3$). It was in the form of a powder having a mean particle size ($\phi_{50}$) of 4.33 µm (measurement by CILAS laser granulometer).

The chromatic coordinates of this control product were the following:

$L^* = 47$ $a^* = 49$ $b^* = 33$ 10 g of the control product prepared above were then introduced into 100 ml of a 10 g/l ammonium fluoride solution. The pH of the mixture thus obtained was then adjusted to a slightly basic value, on the order of 8, by addition of an aqueous ammonia $NH_4OH$ solution (this procedure was to avoid any untimely solubilization of the pigment due to an excessively acidic medium) and the entire mixture was then stirred for 1 hour.

The product was then filtered and dried in a dessicator under vacuum.

The new chromatic characteristics of the product thus obtained were the following:

$L^* = 47$ $a^* = 55$ $b^* = 43$

Its mean particle size ($\phi_{50}$) was 3.67 µm.

This product contained 2.9% by weight of fluorine.

Additionally, X-ray diffraction analyses indicated, inter alia, the presence of the $CeF_3$ phase.

EXAMPLE 2

The reaction was carried out as in Example 1, except that the sodium-doped γ-cubic cerium sesquisulfide $Ce_2S_3$ control product was prepared using a starting mixture in which the Na/Ce molar ratio was 0.25.

10 g of this control product were then fluoridated under the same conditions as those of Example 1.

The chromatic characteristics of the products obtained are reported in Table I below:

TABLE I

| | Before Treatment (control product) | After Treatment (fluoridated product) |
|---|---|---|
| $L^*$ | 41 | 40 |
| $a^*$ | 46 | 54 |
| $b^*$ | 28 | 41 |

EXAMPLE 3

A γ-cubic cerium sesquisulfide $Ce_2S_3$ doped with sodium was prepared by calcining a mixture of cerium oxide and of anhydrous sodium carbonate, the starting Na/Ce molar ratio in the mixture having been set at 0.15, at 800° C. in an argon atmosphere containing carbon sulfide ($CS_2$) in a proportion of a 0.3 bar partial pressure.

10 g of this control product were then fluoridated under the same conditions as those of Example 1.

The characteristics of the products obtained are reported in Table II below:

TABLE II

|  | Before Treatment (control product) | After Treatment (fluoridated product) |
| --- | --- | --- |
| L* | 44 | 45 |
| a* | 48 | 51 |
| b* | 33 | 41 |
| $\phi_{50}$ | 2.6 μm | 2.5 μm |

EXAMPLE 4

Contrary to the above examples (fluoridation via wet process), this example illustrates the invention in the context of a fluoridation treatment via a gas route, using a nitrogen fluoride $NF_3$ plasma.

The principle of the treatment was the following:

The $NF_3$ gas was introduced continuously into a reaction chamber maintained at 80° C. and then dissociated between two electrodes, the species thus formed then diffusing in the said chamber to react with the pigment which was placed beforehand therein. A number of parameters enabled controlling the kinetics and the progress of the fluoridation reaction: the power of the radio frequency generator which effected dissociation of the gas (P), the flow rate of the injected gas (d), the total pressure in the chamber (p) and the duration of the treatment (t). In the present example, the progress of the reaction was monitored experimentally by the increase in weight of the pigment.

0.1 g of the control pigment prepared in Example 2 was thus treated according to the technique described above. The reaction parameters for carrying out this treatment were the following: P1 P=50 W; d=8 cm$^3$/s; p=800 mTorr; $t_{max}$=5 min.

The characteristics of the products obtained ar reported in Table III below:

TABLE III

| Increase in weight (%) | L* | a* | b* |
| --- | --- | --- | --- |
| 0 (before treatment) | 41 | 46 | 28 |
| 1.2 | 39 | 51 | 40 |
| 1.6 | 39 | 53 | 47 |
| 2.1 | 39 | 55 | 46 |

The Auger and ESCA analyses evidenced, for the treated products, a surface enriched in fluorine and in cerium. X-ray diffraction analyses indicated, for their part, the presence of fluoro compounds of $CeF_3$ or CeSF type.

EXAMPLE 5

This example illustrates another embodiment of a fluoridation by a gas route. The pigment was here treated using a gaseous mixture of fluorine ($F_2$) diluted in a neutral gas, nitrogen ($N_2$).

The fluoridation treatment was carried out under static conditions in a nickel reactor containing, at a total pressure of 1 bar, nitrogen in which fluorine was diluted in a proportion of 10% by volume. The temperature of the treatment was 80° C. The maximum treatment duration was set at 2 hours. As in the above example, the progress of the fluoridation reaction was monitored experimentally by the increase in weight of the pigment.

The pigment treated was the control pigment prepared in Example 2.

The characteristics of the products obtained are reported in Table IV below:

TABLE IV

| Increase in weight (%) | L* | a* | b* |
| --- | --- | --- | --- |
| 0 (before treatment) | 41 | 46 | 28 |
| 1.3 | 39 | 54 | 51 |
| 1.7 | 38 | 59 | 50 |
| 2.5 | 40 | 58 | 59 |

The same observations as those made in Example 4 above, regarding the chemical nature of the surface of the treated products, were made.

EXAMPLE 6

This example illustrates the use of a product of the invention for the preparation of a lipstick.

The constituent components of the lipstick were as follows:

TABLE V

| CONSTITUENTS | % BY WEIGHT |
| --- | --- |
| A | |
| Silbione oil 70641 V 200 | 40.5 |
| B | |
| Beeswax | 7.5 |
| Carnauba wax | 3.5 |
| Ozocerite | 3.5 |
| Paraffin wax | 10.0 |
| Liquid paraffin | q.s. for 100 |
| Triglyceride of capric/caprylic acid (*) | 20.0 |
| C | |
| Pigments according to Example 3 | q.s. |
| Titanium dioxide | q.s. |

(*) Myritol 318 from Henkel

The components of Mixture B were melted at a temperature of 85° ±2° C. and then maintained in a thermostatically-controlled bath adjusted to 60° ±2° C.

The pigment and the titanium oxide were mixed with the Silbione oil; this Mixture A/C was placed in a thermostatically-controlled bath (60° ±2° C.).

Mixture B was then added thereto.

The complete mixture was then poured into a silicone lipstick mold.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Fluoridated particulates of a rare earth metal sesquisulfide pigment/colorant.

2. The fluoridated particulates as defined by claim 1, comprising fluorine atoms distributed along a concentration gradient decreasing from the face surfaces to the inner cores thereof.

3. The fluoridated particulates as defined by claim 1, comprising fluorine atoms principally distributed at the outer peripheries thereof.

4. The fluoridated particulates as defined by claim 1, comprising not more than 10% by weight of fluorine atoms with respect to said sesquisulfide.

5. The fluoridated particulates as defined by claim 4, comprising not more than 5% by weight of fluorine atoms with respect to said sesquisulfide.

6. The fluoridated particulates as defined by claim 1, comprising fluoro or sulfofluoro compounds.

7. The fluoridated particulates as defined by claim 6, comprising rare earth metal fluorides and/or sulfofluorides.

8. The fluoridated particulates as defined by claim 1, comprising at least one alkali metal and/or alkaline earth metal dopant, at least in part occluded within the crystal lattices of said sesquisulfide.

9. The fluoridated particulates as defined by claim 8, said at least one dopant being essentially completely occluded within the crystal lattices of said sesquisulfide.

10. The fluoridated particulates as defined by claim 8, said at least one dopant being situated within the cationic gaps of the crystal lattices of said sesquisulfideo.

11. The fluoridated particulates as defined by claim 8, comprising at least 0.1 mol % of said at least one dopant with respect to said rare earth metal.

12. The fluoridated particulates as defined by claim 11, comprising from 5 to 50 mol % of said at least one dopant with respect to said rare earth metal.

13. The fluoridated particulates as defined by claim 8, comprising at least one alkali metal dopant.

14. The fluoridated particulates as defined by claim 13, said at least one alkali metal comprising sodium.

15. The fluoridated particulates as defined by claim 1, said rare earth metal sesquisulfide comprising γ-cubic cerium sesquisulfide $Ce_2S_3$.

16. The fluoridated particulates as defined by claim 15, having an L* chromatic coordinate of at least 30.

17. The fluoridated particulates as defined by claim 16, having an L* chromatic coordinate ranging from 30 to 60.

18. The fluoridated particulates as defined by claim 16, having an a* chromatic coordinate of at least 30.

19. The fluoridated particulates as defined by claim 18, having an a* chromatic coordinate ranging from 35 to 65.

20. The fluoridated particulates as defined by claim 18, having a b* chromatic coordinate ranging from 0 to 40.

21. The fluoridated particulates as defined by claim 1, having a particle size ranging from 1 to 5 μm.

22. The fluoridated particulates as defined by claim 15, comprising a sodium dopant.

23. The fluoridated particulates as defined by claim 1, comprising a cerium sulfide and varying from brown to red in color.

24. The fluoridated particulates as defined by claim 1, comprising a lanthanum sulfide and being yellow in color.

25. The fluoridated particulates as defined by claim 1, comprising a neodymium sulfide and being green in color.

26. The fluoridated particulates as defined by claim 1, comprising a praseodymium sulfide and being yellow-green in color.

27. The fluoridated particulates as defined by claim 1, comprising a dysprosium sulfide and being brown-yellow in color.

28. The fluoridated particulates as defined by claim 1, comprising a terbium sulfide and being ochre in color.

29. The fluoridated particulates as defined by claim 1, comprising an erbium sulfide and being brown in color.

30. The fluoridated particulates as defined by claim 1, comprising a yttrium sulfide and being dark beige in color.

31. The fluoridated particulates as defined by claim 1, comprising a samarium sulfide and being grey-brown in color.

32. The fluoridated particulates as defined by claim 1, comprising a gadolinium sulfide and being green-brown in color.

33. The fluoridated particulates as defined by claim 1, comprising a thullium sulfide and being gold-green in color.

34. The fluoridated particulates as defined by claim 1, having a coating layer of at least one transparent oxide, or hydrate thereof, deposited onto the external face surfaces thereof.

35. The fluoridated particulates as defined by claim 34, said at least one transparent oxide/hydrate comprising silica, alumina, zirconia, zircon, titanium dioxide, or a rare earth metal oxide.

36. The fluoridated particulates as defined by claim 35, said at least one transparent oxide/hydrate comprising silica.

37. The fluoridated particulates as defined by claim 36, said at least one transparent oxide/hydrate consisting essentially of silica.

38. The fluoridated particulates as defined by claim 22, having a coating layer of silica deposited onto the external face surfaces thereof.

39. The fluoridated particulates as defined by claim 34, said coating layer being essentially uniform and of controlled thickness.

40. A process for the preparation of the fluoridated particulates as defined by claim 1, comprising reacting particles of a rare earth metal sesquisulfide with a fluoridating agent.

41. The process as defined by claim 40, comprising fluoridating essentially only the external face surfaces of said particles.

42. The process as defined by claim 40, said fluoridating agent comprising fluorine, a halogen fluoride, ammonium fluoride, a rare gas fluoride, a nitrogen fluoride, a boron fluoride, tetrafluoromethane, hydrofluoric acid, or mixture thereof.

43. The process as defined by claim 42, said fluoridating agent comprising fluorine or ammonium fluoride.

44. The process as defined by claim 40, carried out in liquid or gaseous phase.

45. A pigmented substrate comprising an effective colorant amount of the fluoridated particulates as defined by claim 1.

46. A pigmented substrate comprising an effective colorant amount of the fluoridated particulates as defined by claim 34.

47. The pigmented substrate as defined by claim 45, comprising a colored plastic, resin, paint, varnish, rubber, ceramic, glaze, paper, ink, cosmetic, leather, dye, or coating.

48. The pigmented substrate as defined by claim 47, comprising a nail polish, lipstick, eyeshadow, blush, or foundation cream.

49. The fluoridated particulates as defined by claim 1, wherein the particulates consist of rare earth metal sesquisulfide inner cores surrounded by a fluoro or sulfo-fluoro compound.

* * * * *